US005763494A

United States Patent [19]
Balandrin et al.

[11] Patent Number: 5,763,494
[45] Date of Patent: *Jun. 9, 1998

[54] PHARMACEUTICAL COMPOSITIONS COMPRISING ISOVALERAMIDE

[75] Inventors: Manuel F. Balandrin; Bradford C. Van Wagenen, both of Salt Lake City, Utah

[73] Assignee: NPS Pharmaceuticals, Inc., Salt Lake City, Utah

[*] Notice: The term of this patent shall not extend beyond the expiration date of Pat. No. 5,506,268.

[21] Appl. No.: 623,691

[22] Filed: Mar. 29, 1996

Related U.S. Application Data

[63] Continuation of Ser. No. 75,126, Jun. 11, 1993, Pat. No. 5,506,268.

[51] Int. Cl.$^6$ ............................. A01N 37/18; A61K 31/13
[52] U.S. Cl. ............................................... 514/629; 514/923
[58] Field of Search ................................... 514/629, 923

[56] References Cited

U.S. PATENT DOCUMENTS

| | | | |
|---|---|---|---|
| 4,205,083 | 5/1980 | Thies | 424/283 |
| 4,246,282 | 1/1981 | Chignac et al. | 424/320 |
| 4,391,819 | 7/1983 | Thies et al. | 424/278 |
| 4,814,183 | 3/1989 | Zentner | 424/485 |
| 5,147,857 | 9/1992 | Raddatz et al. | 514/19 |
| 5,300,507 | 4/1994 | Yous et al. | 514/253 |

OTHER PUBLICATIONS

Allport, N.L., ed., *The Chemistry and Pharmacy of Vegetable Drugs* Chemical Publishing Company, Inc., Brooklyn, New York, (1944) pp. 159–161.

Bringmann, G., "A first biosynthetic proposal for the in vivo formation of naturallly occuring diazepam–like 1,4–benzodiazepines", *J. Neural. Trans.* (1992) 88: 77–82.

Burger, A., ed., *Medicinal Chemistry* Interscience Publishers, Inc., New York, New York, (1951) vol. I, pp. 113–114 and 128–137.

Burger, A., ed., *Medicinal Chemistry* 2nd Edition, Interscience Publishers, Inc., New York, New York, (1960) vol. II, pp. 357–359, 362, 369, 370–375.

Burger, A., ed., *Medicinal Chemistry* 3rd Edition, Wiley–Interscience, New York, New York, (1970) vol. II, pp. 1365–1394, 1397–1401.

Burtner, R.R., et al., "The hypnotic properties of some derivatives of trihalogenated alcohols", *J. Pharmacol. Exptl. Therap.* (1938) 63: 183–192.

Byrum, W.R., et al., "Preliminary pharmacological studies of some amides of choral and alpha, alpha, beta–Trichlorobutyraldehyde" *J. Am. Pharm. Assoc., Sci. Ed.* (1952) 41: 100–102.

Case, J.D., et al., "Sedormid–induced porphyria in the rat" *Proc. Soc. Exptl. Biol. Med.* (1953) 83: 566–568.

Childress, S.J., "Antianxiety agents" *Burger's Medicinal Chemistry*, Part III, 4th Edition, Wolff, M.E., ed., John Wiley & Sons (Wiley–Interscience), New York, New York, (1981) pp. 981–996.

Christmas, A.J., et al., "A comparison of the effects of some benzodiazepines and other drugs on aggressive and exploratory behaviour in mice and rats" *Neuropharmacology* (1979) 9: 17–29.

de Barreiro, O.C., "Effect of sedormid chlorpromazine, and iproniazid on the activity of UDP–glucuronate glucuronyl transferase in rat liver: A histological study" *Biochem. Pharmacol.* (1965) 14: 1694–1696.

(List continued on next page.)

*Primary Examiner*—C. H. Kelly
*Attorney, Agent, or Firm*—Foley & Lardner

[57] ABSTRACT

Isovaleramide has been found to exhibit mild anxiolytic activity at low to moderate dosage levels and mildly sedative at somewhat higher dosage levels. In contrast to certain other materials thought to be anxiolytic or mildly sedative, isovaleramide is non-cytotoxic and does not paradoxically stimulate the central nervous system. Isovaleramide is therefore useful as a mild anxiolytic and mild sedative which can be made available to the general public.

7 Claims, 4 Drawing Sheets

ISOVALERAMIDE

ISOVALERIC ACID

VALINE

VALYL

VALNOCTAMIDE

NEODORM n-VALERAMIDE

VALPROMIDE

VALPROIC ACID

OTHER PUBLICATIONS

Eeckhout, A.V.D., "The hypnotic action of members of the valerianic acid group" *Chem. Abstr.* (1908) 2: 668.

Eeckhout, A.V.D., "Studien über die hypnotische wirkung in der valerian-säuregruppe" *Arch. Exptl. Pathol. Pharmako.* (1907) 57: 338–357.

Foye, W.O., ed., *Principles of Medicinal Chemistry* 3rd Edition, Les & Febiger, Philadelphia, Pennsylvania, (1989), Chapter 8, pp. 143–237.

Gilman, A.G., et al., eds., *The Pharmaceutical Basis of Therapeutics* 8th Edition, Permagon Press, New York, New York, (1990) pp. 345–346, 436, 450–453.

Goldberg, A., et al., "Experimentally produced porphyria in animals" *Proc. Roy. Soc. Ser. B. (Biol. Sci.)* (1955) 143: 257–280.

Goldberg, A., et al., eds., *Diseases of Porphyrin Metabolism* Charles C. Thomas Publishers, Springfield, Illinois (1962) Chapter VIII, pp. 175–199.

Goldberg, M., et al., "Effects of a new tranquilizer, vamethamide, in psychiatric outpatient card" *Dis. Nerv. Syst.* (1961) 22: 346–348.

Granick, S., "Hepatic porphyria and drug-induced or chemical porphyria" *Ann. N.Y. Acad. Sci.* (1965) 123: 188–197.

Grier, J., "Valerian: its history, constituents and uses" *Chemist Druggist* (1929) 110: 420–422.

Hare, H.A., et al., eds., The National Standard Dispensatory Lea Brothers, Inc., New York, New York (1905), pp. 93–94, 129–130, 159–160, 169, 550, 642, 692–693, 1031, 1426, 1480, 1571–1572, 1619–1620, 1631, 1633, 1661–1662.

Hirsch, G.H., et al., "Studies of the relationship between chemical structure and porphyria-inducing activity-III," *Biochem. Pharmacol.* (1967) 16(18): 1455–1462.

Hirsch, G.H., et al., "Studies of the relationship between chemical structure and porphyria-inducing activity-II," *Biochem Pharmacol.* (1967) 15: 1006–1008.

Hobbs, C., "Valerian, a literature review" *Herbalgram* (1989) No. 21, pp. 19–34 and No. 23, pp. 4 and 47–48.

Houghton, P.J., "The biological activity of valerian and related plants" *J. Ethnopharmacology* (1988) 22: 121–142.

Impens, E., "Pharmakologisches über luminal oder phenyläthybarbitursäure" *Deut. Med. Worchschr.* (1912) 38: 945–947.

Irwin, S., "Comprehensive observational assessment: La. A systematic, quantitative procedure for assessing the behavioral and physiologic state of the mouse" *Physchopharmacologia* (1968) 13: 222–257.

Jenkins, G.L., et al., *The Chemistry of Organic Medicinal Products* 2nd Edition, John Wiley & Sons, Inc., London, England, (1943) pp. 214–215, 374–383, and 616–621.

Junkmann, K., "Studien über die hypnotische wirkung substituierter acetamide" *Arch. Exptl. Pathol. Pharmako.* (1937) 186: 552–564.

Junkmann, K., "Einiges über spasmolytica" *Arch. Exptl. Pathol. Pharmako.* (1940) 195: 175–183.

Klotz, U., et al., "Occurrence of 'natural' benzodiazepines" *Life Sci.* (1991) 48: 209–215.

Krieglstein, V.J., et al., "Zentral dämpfende inhaltsstoffe im bladrian" *Deut. Apoth. Zeitung* (1988) 128: 2041–2046.

Marks, G.S., et al., "Studies of the relationship between chemical structure and porphyria-inducing activity" *Biochem. Pharmacol.* (1965) 14: 1077–1084.

Marks, P.A., et al., "Drug-induced hemolytic anemias associated with glucose-6-phosphate dehydrogenase deficiency: A genetically heterologous trait" *Ann. N.Y. Acad. Sci.* (1965) 123: 198–206.

May, P., *The Chemistry of Synthetic Drugs* Longmans, Green and Company, London, England (1921) pp. 24–25, 186–188, 234–235.

Meyer, K.H., et al., "Beiträge zur theorie der narkose" *Biochem. Z.* (1935) 277: 39–71.

Nelson, J.W., et al., "A pharmaceutical study of some new synthetic hypnotics" *J. Am. Pharm. Assoc., Sci. Ed.* (1941) 30: 180–182.

Petersen, E.N., et al., "A water lick conflict paradigm using drug experienced rats" *Psychopharmacology* (1981) 75: 236–239.

Richards, A.N., "Pharmacology of luminal or phenylethylbarbituric acid" *Chem. Abstr.* (1912) 6: 2109–2110.

Rosecrans, J.A., et al., "Pharmacological investigation of certain *Valeriana officinalis* L. extracts" *J. Pharm. Sci.* (1961) 50(3): 240–244.

Roszkowski, A.P., et al., "Behavioral and central muscle relaxant properties of 2-ethyl-3-methylvaleramide" *Int. J. Neuropharmacol.* (1962) 1: 423–430.

Samson, F.E., Jr., et al., "A study on the narcotic action of the short chain fatty acids" *J. Clin. Invest.* (1956) 35(2): 1291–1298.

Schmid, R., et al., "Experimental porphyria. III. Hepatic type produced by sedormid" *Proc. Soc. Exptl. Biol. Med.* (1952) 81: 685–689.

Schneck, D.W., et al., "Studies of the relationship between chemical structure and porphyria-inducing activity-IV," *Biochem. Pharmacol.* (1968) 17(7): 1385–1399.

Schneck, D.W., et al., "Studies of the relationship between chemical structure and porphyria-inducing activity-V." *Biochem. Pharmacol.* (1972) 21(7): 2509–2518.

Sepinwall, J., et al., "Behavioral pharmacology of antianxiety drugs" *Handbook of Psychopharmacology* Plenum Press, New York, New York, Iverson, L.L., et al., eds., (1978) vol. 13, chap. 6, pp. 345–393.

Slater, I.H., et al., "Diethylbutanediol, a convulsant homologue of the depressant, diethylpropanediol" *J. Pharmacol. Exptl. Therap.* (1954) 111: 182–196.

Stepansky, W., "A clinical study in the use of valmethamide, an anxiety-reducing drug" *Curr. Ther. Res.* (1960) 2: 144–147.

Talman, E.L., et al., "Porphyrin metabolism. IV. Molecular structure of acetamide derivatives affecting porphyrin metabolism" *Arch. Biochem. Biophys.* (1957) 66: 289–300.

Talman, E.L., et al., "Porphyrin metabolism. I. Experimental porphyria in chick embryos" *J. Bio. Chem.* (1955) 212: 663–675.

Teychenne, P.F., et al., "The encephalopathic action of five-carbon-atom fatty acids in the rabbit" *Clin. Sci. Mol. Med.* (1976) 50(6): 463–472.

Unseld, E., et al., "Detection of desmethyldiazepam and diazepam in brain of different species and plants" *Biochem. Pharmacol.* (1989) 38(15): 2473–2478.

Volwiler, E.H., et al., "Some alkyl and aryl amides and ureides as hypnotics" *J. Amer. Chem. Soc.* (1936) 58: 1352–1354.

Wagner, H., et al., "In vitro–und in vivo–metabolismus von $^{14}$C–didrovaltrat" *Planta Med.* (1980) 38: 366–376.

Wildmann, J., et al., "occurence of pharmacologically active benzodiazepines in trace amounts in wheat and potato" *Biochem. Pharmacol.* (1988) 37(19): 3549–3559.

Wildmann, J., "Increase of natural benzodiazepines in wheat and potato during germination" *Biochem. Biophys. Res. Commun.* (1988) 157(3): 1436–1443.

Wildmann et al., "Diazepam and N–desmethyldiazepam are found in rat brain and adrenal and may be of plant origin" *J. Neural. Trans.* (1987) 70: 383–398.

Wilson, O.C., et al., eds., *Organic Chemistry in Pharmacy* J.B. Lippincott Company, Philadephia, Pennsylvania, (1949) pp. 1–2, 117, 128–135.

Wolff, M.E., ed., *Burger's Medicinal Chemistry* 4th Edition, Wiley–Interscience, New York, New York, (1981) Part III, pp. 787–828.

*1929 Year Book of the American Pharmaceutical Association* American Pharmaceutical Association Publishers, Baltimore, Maryland (1931) vol. 18, pp. 154–155, 190–191, 244–245.

*1931 and 1932 Year Book of the American Pharmaceutical Association* American Pharmaceutical Association Publishers, Washington, D.C. (1934) vol. 20–21, pp. 110–111, 154–155, 318–319.

*The Merck Index* (1989) 11th Edition, #5118–#5124.

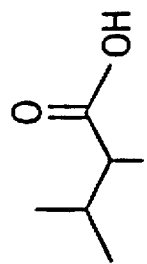 VALINE
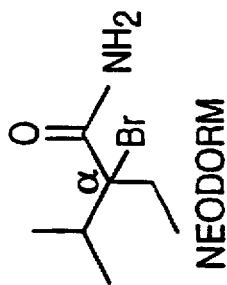 NEODORM
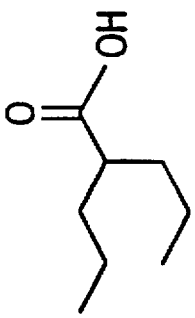 VALPROIC ACID
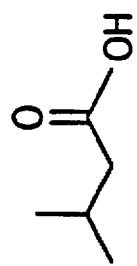 ISOVALERIC ACID
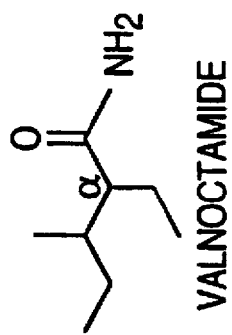 VALNOCTAMIDE
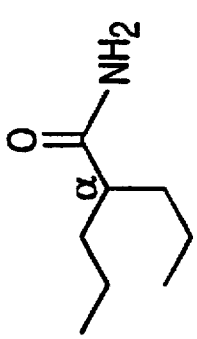 VALPROMIDE
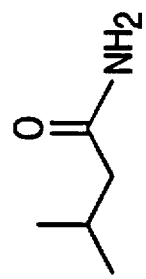 ISOVALERAMIDE
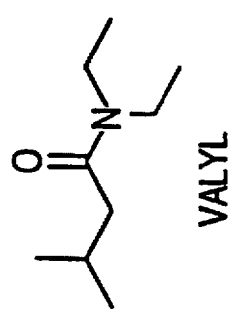 VALYL
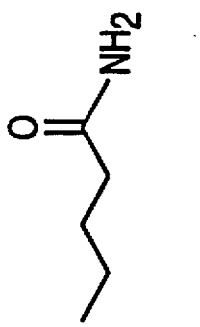 n-VALERAMIDE
*FIG. 1*

PHARMACEUTICAL COMPOSITIONS COMPRISING ISOVALERAMIDE

CROSS-REFERENCE TO RELATED APPLICATIONS

This application is a continuation application of application U.S. Ser. No. 08/075,126, filed Jun. 11, 1993, now U.S. Pat. No. 5,506,268, which issued on Apr. 9, 1996.

TECHNICAL FIELD

The invention relates to methods to reduce anxiety without producing undesirable excessive sedation in animal, including human, subjects. More particularly, it concerns the use of isovaleramide as a mild anxiolytic and sedative agent in humans.

BACKGROUND ART

The complex interrelationships of the receptors, neurotransmitters, and electrical impulses which affect the central nervous system are far from being fully understood. However, it has been possible to distinguish the effects of various pharmaceuticals and other drugs on aspects of the central nervous system that are exhibited as behaviors.

In particular, it is possible to distinguish an anxiolytic effect from a sedative one. Standard behavioral tests, such as the exploratory behavior test and the Vogel Conflict Paradigm described below can demonstrate and quantify the anxiolytic effects of various pharmaceutical agents. Other tests, including the prolongation of barbiturate-induced sleep time and the induction of sleep, show sedative and hypnotic effects, respectively.

While some agents are effective in inducing both anxiolysis and sedation, other agents, often structurally closely related, can be shown to exhibit primarily only one or the other activity. Moreover, the ability of useful antianxiety agents to exhibit primarily either anxiolytic or sedative activities is often related to dose (Wolff, M. E. (Ed.) *Burger's Medicinal Chemistry*, Part III, 4th ed. (1981) Wiley-Interscience, pp. 981–996; Foye, W. O. (Ed.) *Principles of Medicinal Chemistry*, 3rd ed. (1989) Lea and Febiger, pp. 143–237). Furthermore, there are additional demonstrable possible effects on the central nervous system such as the ability to induce or repress convulsions. Again, various structurally related compounds may or may not exhibit these abilities. What is clear from the art available at present is that there seem to be no clear structure-function correlations that can be made with respect to predicting the ability of a particular substance to affect or not affect the central nervous system in a prescribed manner.

The invention herein concerns the use of isovaleramide as a mild anxiolytic, and, at higher doses, as a mild sedative. It has been shown, as will be described hereinbelow, that these two effects of isovaleramide can be separated and emphasized based on dosage level.

FIG. 1 shows the structures of various known compounds which are structurally related to isovaleramide. In addition, as isovaleramide was initially prepared herein from extracts of the underground parts of *Valeriana officinalis* L. (common name: valerian) and extracts of this plant have been used historically as sedatives and antispasmodics, it is germane to indicate what is known about valerian extracts in this regard, as well as to discern the art concerning the compounds of FIG. 1.

The extracts of certain medicinal plants have been used for the reduction of stress and for the treatment of anxiety in many different cultures throughout the world since time immemorial, and a number of anxiolytic and sedative principles have been isolated from higher plants and characterized in modern times. Indeed, benzodiazepine tranquilizer compounds such as diazepam ("VALIUM"), oxazepam ("SERAX"), and lorazepam ("ATIVAN"), which have been considered to represent the quintessential synthetic anxiolytic agents par excellence, have now been shown unequivocally to be naturally occurring plant-derivable compounds, having been found in potatoes, soybeans, lentils, corn, wheat, buckwheat, rice, oats, barley, and millet (Wildmann et al., *J. Neural Transm.* (1987) 70:383–398; Wildmann, J. *Biochem. Biophys. Res. Commun.* (1988) 157:1436–1443; Wildmann et al., *Biochem. Pharmacol.* (1988) 37:3549–3559; Unseld et al., *Biochem. Pharmacol.* (1989) 38:2473–2478; Klotz, U., *Life Sci.* (1991) 48:209–215; Bringmann, G., *J. Neural Transm.* (1992) 88:77–82).

The use of valerian extracts for medicinal purposes has centuries of history behind it, but the active components have not been clearly or positively identified (Krieglstein, J. and D. Grusla, *Deut. Apoth. Ztg.* (1988) 128:2041–2046), nor has the nature of the effect of the extracts been clearly characterized and segregated into behaviorally distinguishable effects. The roots of valerian contain three principal classes of compounds: (a) the volatile oil(s), which are composed primarily of isovaleric acid and volatile monoterpenoid and sesquiterpenoid derivatives, (b) non-volatile monoterpenoid iridoids or valepotriates, and (c) monoterpenoid alkaloids. The monoterpenoid alkaloids are only minor components and are not considered to contribute significantly to the effects of valerian; similarly, the volatile oil fraction seems only weakly active. Attention has therefore focused on the valepotriate fraction, which is generally comprised of monoterpenoid (iridoid) esters. These esters are water insoluble, and cannot contribute entirely to the plant's sedative effect since aqueous extracts of valerian root exhibit sedative activity. The valepotriates may also be toxic (see below).

Recent studies on the valepotriates have shown that these compounds can irreversibly alkylate DNA and proteins and that small quantities of orally administered valepotriates actually reach the mouse brain and other organs intact (Wagner, H. and K. Jurcic, *Planta Med.* (1980) 38:366–376). However, in spite of this potentially hazardous toxicity, the valepotriate fractions have been marketed extensively as sedatives in Europe.

Ammoniated tinctures of valerian have also been used in the United States and Great Britain as sedatives, but only as crude mixtures.

The activities of chemically defined agents intended to affect the central nervous system show an interesting lack of pattern. Isovaleric acid, isovaleramide and related substances are known to elicit narcotic and hypnotic effects in experimental animals when administered in very high doses (Eeckhout, A.v.d., *Arch. exptl. Pathol. Pharmakol.* (1907) 57:338–357; Impens, E., *Deut. med. Wochschr.* (1912) 38:945–947; May, P., *The Chemistry of Synthetic Drugs*, 3rd ed. (1921) Longmans, Green and Co., p. 24; Meyer, K. H. and H. Hemmi, *Biochem. Z.* (1935) 277:39–71; Junkmann, K., *Naunyn-Schmiedeberg's Arch. exptl. Pathol. Pharmakol.* (1937) 186:552–564; Samson et al., *J. Clin. Invest.* (1956) 35:1291–1298; Teychenne et al., *Clin. Sci. Molec. Med.* (1976) 50(6):463–472). Furthermore, salts of isovaleric acid were used as sedatives in the early twentieth century, but it was considered that their effect was psychological and due to the stench of the highly volatile free acid (Hare et al., *The*

National Standard Dispensatory (1905) Lea Brothers and Co., pp. 94, 159–160, 1619–1620; Grier, J., Chem. Drug. (1929) 110:420–422; Allport, N. L., The Chemistry and Pharmacy of Vegetable Drugs (1944) Chemical Publishing Co., pp. 159–161; Year Book of the American Pharmaceutical Association, 1912 (1914) 1: pp. 178–179; De Re Medicina (1938) Eli Lilly and Co., p. 159). Isovaleramide itself was shown to exhibit hypnotic activity only when administered to experimental animals in very high doses and was considered to be clinically useless as a hypnotic (Impens, E., Deut. med. Wochschr. (1912) 38:945–947; Junkmann, K., Naunyn-Schmiedeberg's Arch. exptl. Pathol. Pharmakol. (1937) 186:552–564). A series of α-brominated and/or α-alkylated isovaleramide derivatives, however, were considered successful in this regard (Volwiler, E. H. and D. L. Tabern, J. Am. Chem. Soc. (1936) 58:1352–1354; Burger, A., Medicinal Chemistry, Vol. 1, (1951) Interscience, pp. 131–132; Burger, A. (Ed.) Medicinal Chemistry, 2nd ed. (1960) Interscience, pp. 357–375; Burger, A. (Ed.), Medicinal Chemistry, Part II, 3rd ed. (1970) Wiley-Interscience, pp. 1365–1385; Wolff, M. E. (Ed.) Burger's Medicinal Chemistry, Part III, 4th ed. (1981) Wiley-Interscience, pp. 787–828).

Valnoctamide (see FIG. 1) is one such compound. Valnoctamide is a synthetic, barbiturate-derived, α-branched, water-insoluble compound which is purported to exhibit tranquilizing and anxiety-reducing properties which can quiet aggressive experimental animals and anxious humans (Stepansky, W., Curr. Therap. Res. (1960) 2:144–147; Goldberg, M., Dis. Nerv. Syst. (1961) 22:346–348; Roszkowski, A. P. and W. M. Govier, Int. J. Neuropharmacol. (1962) 1:423–430), and which produces hypnosis in rats at doses of 250 mg/kg IP. Although valnoctamide may appear superficially to be structurally similar to isovaleramide, there are considerable physicochemical and pharmacological differences between the two compounds. For example, valnoctamide is very water insoluble, while isovaleramide is essentially water soluble. Furthermore, valnoctamide exhibits pronounced hypnotic properties in rats at relatively low doses (e.g., 250 mg/kg [1.75 mM/kg] IP), whereas isovaleramide is not hypnotic in mice even in doses as high as 1000 mg/kg (9.90 mM/kg) IP, and exhibits hypnotic activity only at near-toxic dose levels (2000 mg/kg IP and higher). Thus, the pharmacological profile of valnoctamide appears to more closely resemble that of its synthetic barbiturate precursor than that of isovaleramide.

Valnoctamide contains two (chiral) stereocenters (the branched α and β carbons); isovaleramide possesses no (chiral) stereocenters. Thus, "valnoctamide" is actually a mixed racemic preparation consisting of four stereoisomers in two diastereoisomeric sets of enantiomers. It is not known whether all four of these stereoisomeric forms are pharmacologically equivalent. We have demonstrated (by means of carbon-13 nuclear magnetic resonance [$^{13}$C-NMR] spectroscopy) that these two diastereomeric sets of enantiomers exist in unequal amounts in "valnoctamide". Since isovaleramide possesses no optically active (chiral) stereocenters, it exists as a single, clearly definable molecular entity with no alternative enantio- or diastereoisomeric forms, and its experimentally determined pharmacological properties and profile are those of a single, pure molecular entity.

Doses of isovaleramide as relatively low as 30–100 mg/kg IP in mice exhibit quantifiable CNS-depressant effects. Since the $LD_{50}$ value of isovaleramide is greater than 4000 mg/kg IP in mice, the therapeutic index of the compound appears to be on the order of 40. A comparable value for valnoctamide is on the order of 11.4 (Roszkowski, A. P. and W. M. Govier, Int. J. Neuropharmacol. (1962) 1:423–430). Since valnoctamide is a barbiturate-derived compound, it shares some of the undesirable (in this case) properties of certain barbiturates, such as true hypnotic potential.

In addition, certain α-branched isovaleramide derivatives which are very closely structurally related to valnoctamide have been shown to exhibit a potential for producing hepatic porphyria (see, for example, Schmid, R. and S. Schwartz, Proc. Soc. Exptl. Biol. Med. (1952) 81:685–689; Case et al., Proc. Soc. Exptl. Biol. Med. (1953) 83:566–568; Goldberg, A., Biochem. J. (1954) 57(1):ii; Goldberg et al., Proc. Roy. Soc., Ser. B. (Biol. Sci.) (1955) 143:257–280; Talman et al., J. Biol. Chem. (1955) 212:663–675; Talman et al., Arch. Biochem. Biophys. (1957) 66:289–300; Goldberg, A. and C. Rimington, Diseases of Porphyrin Metabolism (1962) Charles C. Thomas, pp. 175–199; Granick, S., Ann. N. Y. Acad. Sci. (1965) 123:188–197; Marks et al., Biochem. Pharmacol. (1965) 14(7):1077–1084; de Barreiro, O. C., Biochem. Pharmacol. (1965) 14:1694–1696; Hirsch et al., Biochem. Pharmacol. (1966) 15(7):1006–1008; Hirsch et al. Biochem. Pharmacol. (1967) 16(8):1455–1462; Schneck et al., Biochem. Pharmacol. (1968) 17(7):1385–1399; Schneck, D. W. and G. S. Marks, Biochem. Pharmacol. (1972) 21(18):2509–2518), also a property shared in common with certain barbiturates, while isovaleramide has no hepatic porphyria-inducing properties, presumably because of a lack of steric hindrance at the α position to ready amide hydrolysis by liver enzymes (Hirsch et al., Biochem. Pharmacol. (1966) 15(7):1006–1008; Hirsch et al. Biochem. Pharmacol. (1967) 16(8):1455–1462; Schneck, et al., Biochem. Pharmacol. (1968) 17(7):1385–1399; Schneck, D. W. and G. S. Marks, Biochem. Pharmacol. (1972) 21(18):2509–2518).

Neodorm (see FIG. 1) has also been marketed as a sedative-hypnotic agent (Year Book of the American Pharmaceutical Association, 1929 (1931) 18:154); Year Book of the American Pharmaceutical Association, 1931 and 1932 (1934) 20,21:154). Several reports erroneously identify Neodorm as α-ethyl isovaleramide; however, it is known that the α-brominated structure shown in FIG. 1 is in fact the correct structure.

Derivatization (N-alkylation) of the nitrogen atom of the amide group has produced compounds such as N,N-diethylisovaleramide (A. Liebrecht, German Patent 129,967, issued 1902) which has been marketed as a sedative. However, this compound is shown hereinbelow to exhibit CNS-stimulating, anxiogenic, and convulsant properties. Indeed, N-methylated amide derivatives can show either CNS-stimulating or -depressing properties, whereas N-ethyl and larger derivatives generally possess CNS-stimulating properties (Volwiler, E. H. and D. L. Tabern, J. Am. Chem. Soc. (1936) 58:1352–1354; Nelson et al., J. Am. Pharm. Assoc., Sci. Ed. (1941) 30:180–182). This is analogous to the effect of addition or subtraction of methyl or methylene groups in other CNS agents such as catecholamine- and serotonin-like agents (F. W. Schueler (Ed.) Molecular Modification in Drug Design, Advances in Chemistry Series No. 45 (1964) American Chemical Society, pp. 114–139), the barbiturates (Burger, A. (Ed.) Medicinal Chemistry, Part II, 3rd ed. (1970) Wiley-Interscience, pp. 1365–1385), and other compound classes (Slater et al., J. Pharmacol. Exptl. Therap. (1954) 111:182–196), which can then exhibit either CNS-depressing or -stimulating properties.

Additional related compounds, valproic acid and valpromide (see FIG. 1) have been used as antiepileptic (anticonvulsant) drugs (Gilman et al. (Eds.) Goodman and

*Gilman's The Pharmacological Basis of Therapeutics*, 8th ed. (1990) Pergamon Press, pp. 436–462). However, isovaleramide itself has no anticonvulsant properties.

Thus, it is readily seen that there are no clearly discernible structure-function relationships which permit predictability of compounds which will affect the central nervous system in the experimentally distinguishable outcomes described hereinbelow. The finding that isovaleramide can be a useful mild anxiolytic agent and mild sedative at prescribed doses makes it a useful addition to the repertoire of available psychotherapeutic agents.

DISCLOSURE OF THE INVENTION

The invention is directed to the use of isovaleramide as an active ingredient in pharmaceutical compositions which are mildly anxiolytic at low dosage levels and mildly sedative at somewhat higher dosage levels. Isovaleramide does not produce undesirable sedative effects at the lower dosages, nor does it behave as a hypnotic. It is also relatively nontoxic.

Accordingly, in one aspect, the invention is directed to a method to reduce anxiety in animal and human subjects which method comprises administering isovaleramide or a pharmaceutical composition thereof to a subject in need of such treatment at an effective dosage to produce this effect. In another aspect, the invention is directed to a method to induce mild sedation by administering isovaleramide at a somewhat higher dosage level. The invention is also directed to pharmaceutical compositions useful in the foregoing methods, especially oral compositions.

BRIEF DESCRIPTION OF THE DRAWINGS

FIG. 1 shows the chemical structures, generic and trade names, and uses of isovaleramide and structurally related known compounds.

MODES OF CARRYING OUT THE INVENTION

Figure 2:
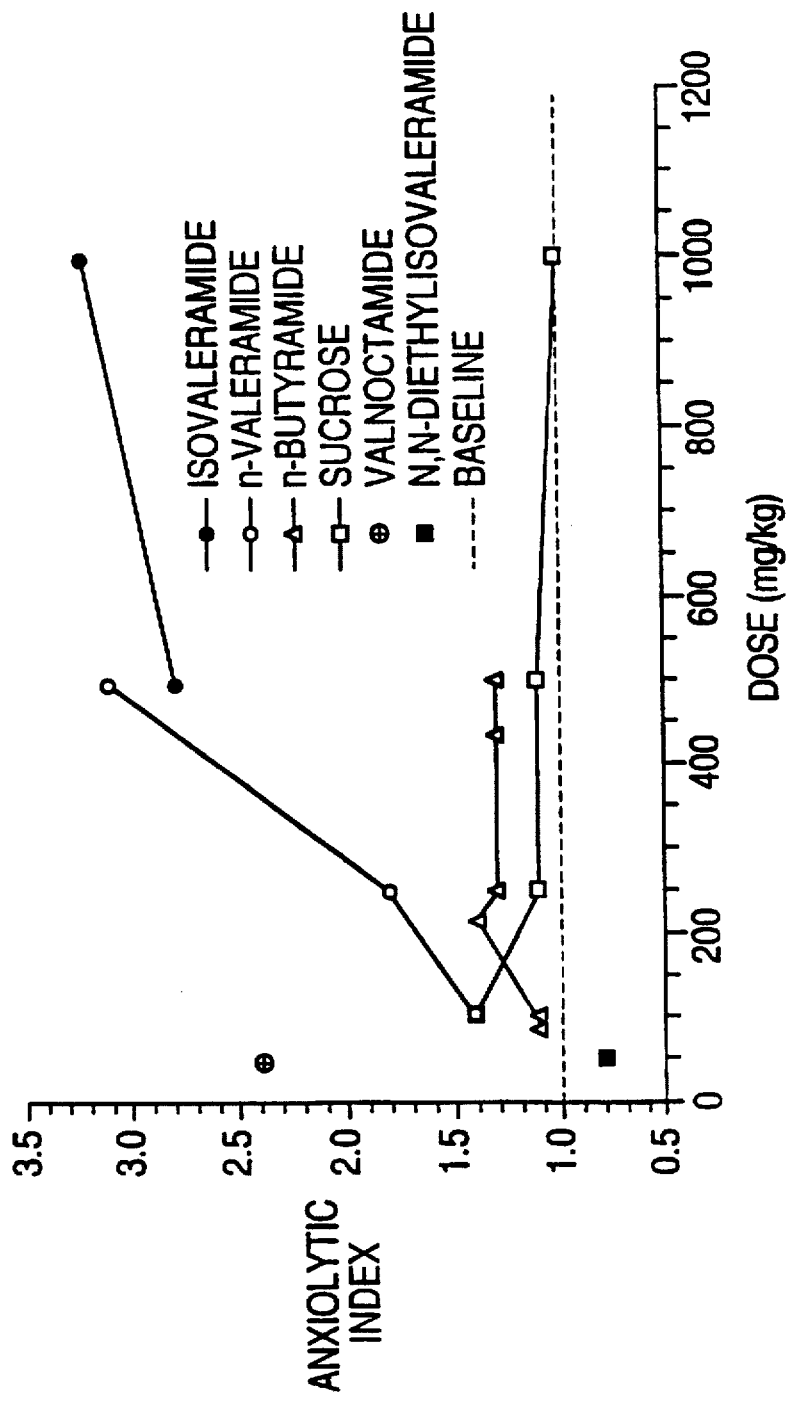
FIG. 2 shows the anxiolytic activity of isovaleramide and structurally related and control compounds derived from Vogel assay data from male rats and expressed as an anxiolytic index.

The invention concerns the use of isovaleramide specifically to induce mild anxiolysis and mild sedation, depending on the dosage. The ability of isovaleramide to exert these effects without undesirable side effects is a major feature of its utility. It is therefore important to distinguish between the various behavioral outcomes which can be experimentally determined as a result of administering agents which affect the central nervous system. Some of these behaviors and tests which assess them are as follows:
Anxiolytic Activity An anxiolytic effect can be measured using either the exploratory behavior test or the Vogel Conflict Paradigm.

The exploratory behavior test (Christmas, A. J. and D. R. Maxwell, *Neuropharmacology* (1970) 9:17–29; Sepinwall, J. and L. Cook, *Handbook of Psychopharmacology* (1978) 13:345–393) is conducted by measuring an increase or decrease of locomotor activity when the animal is placed in a novel or familiar environment. Anxiolytic agents increase exploratory behavior in a novel environment, but do not affect behavior in a familiar environment.

In one form of the test, wooden chambers (65 cm×100 cm×20 cm) with a wire-mesh floor and phototubes 3 cm from the floor are used. The phototubes are arranged in a grid and register the animal crossings through a break in the light path. The phototube output is fed to a computer (IBM) for storage and data analysis. Activity is quantified by counting the total number of crossings and the number of crossings per unit time.

Sprague-Dawley male rats are injected intraperitoneally (IP) with either the test or control substance and are then placed into the activity chambers. They are observed for 1 hr. This will be a novel environment to them. Locomotor activity during the initial 5 min is increased by anxiolytic agents.

At the end of the first trial, the animals are removed and allowed to recover in the animal colony for 7 days, and then placed in the same activity chambers for 1 hr on days 8 and 9. By this time, it is considered that the environment is familiar to the test animals. Injection of the test substance or control on day 10 and repetition of the experiment thus gives results in a familiar environment.

In the Vogel Conflict Paradigm, thirsty rats are given mild electric shocks through a metal water dispenser when they try to drink. The shock is unpleasant, but not severe enough to cause overt pain. When administered anxiolytic drugs, the rats lick the dispenser more often than controls. Assessment of anxiolytic effects is thus measured as an increased number of licks.

As used hereinbelow, a modified form of the standard Vogel assay (Petersen, E. N. and J. B. Lassen, *Psychopharmacology* (1981) 75:236–239) is used. Animals (male Sprague-Dawley rats, 250–300 g) are deprived of water for 24 hr and are then placed into a clear Plexiglass box (45 cm×25 cm×20 cm) which rests on a grid of stainless steel bars. A circuit between the grid bars and the drinking spout is established with a silver electrode in a drinking bottle placed in the chamber. The animals are allowed to lick the water dispenser for 5 min without shock; those animals that fail to lick are excluded from further study.

The animals are returned to the home colony and are again deprived of water for 24 hr and replaced in the chamber and allowed to lick for 1 min without shock. Then a 1 milliamp current (shock) is maintained for 4 min at the drinking spout. Only the animals showing 50% suppression in licking behavior compared to the first session are included in further testing.

The test substances are injected intraperitoneally (IP) after this session, and 30 min later the animals are again placed into the chamber. Again the animals are allowed to lick without shock for 1 min and the shock is instituted for the remaining 4 min. The number of punished licks during this time is used to assess anxiolytic activity.

Both of the foregoing assays show anxiolytic activity. In the first assay, sedatives show no activity, whereas in the Vogel Conflict Test sedatives also give positive results.
Sedative Activity Sedative effects can be measured by the prolongation of the time of barbiturate-induced sleep. In this assay, animals are injected IP with the test compound or control and 15 or 30 min later injected IP with 50 mg/kg pentobarbital sodium. The animals are then placed in a small Plexiglass chamber in a behavioral testing room and the latency to sleep and duration of sleep are recorded manually. The onset of sleep is defined as occurring when the animal loses the ability to right itself when placed on its side (Irwin, S., *Psychopharmacologia* (1968) 13:222–257). The duration of sleep is defined as the interval occurring between loss and recovery of the righting reflex.

Hypnotic Activity

Hypnotic activity was assessed by simply determining the doses of the test substances (administered by IP injection) sufficient to cause a loss of the righting reflex (see above) and an apparent loss of consciousness and responsiveness. This is considered to represent the "induction of sleep", and is clearly distinguishable from a sedative effect in which the experimental animals are merely slowed or rendered sluggish in their behaviors, but retain the righting reflex to some degree, as well as some measure of responsiveness.

Characteristics of Isovaleramide

The effect of isovaleramide in the assays for various CNS effects, combined with its lack of toxicity, make it an ideal mild anxiolytic and, at higher dosages, a mild sedative. Thus, isovaleramide is useful in treating persons suffering from symptoms of mild anxiety, including tension, restlessness, nervousness, inability to concentrate, over-aggressiveness, irritability, and insomnia. Other conditions and therapeutic regimens which may benefit from the anxiolytic effects of isovaleramide include the treatment of the symptoms of smoking cessation, treatment of alcoholism and other substance abuse, premenstrual syndrome, menstrual discomfort, and hyperexcitability in children.

For an over-the-counter-type formulation, an oral route of administration is preferred and is preferably achieved via solid dosage forms such as enteric-coated tablets, caplets, or capsules, or liquid dosage forms such as syrups or elixirs. The indicated dosage of isovaleramide as an anxiolytic is on the order of 100–1000 mg per adult, preferably 100–500 mg per 60–70 kg adult. This amounts to about 1.5–20 mg/kg, preferably about 1.5–10 mg/kg. Unit solid oral dosage forms generally contain about 250 mg/tablet or capsule, which are taken 1–2 at a time for a maximum of 4 times per day. Liquid formulations can also be employed with active ingredient compositions so as to provide 1–2 teaspoonfuls per dose. Furthermore, corresponding reduced dosage pediatric chewable and liquid oral dosage forms can also be developed. This compound can also be added to foods and beverages in the form of drops (with a dropper from a "concentrate" preparation) for oral administration. In addition, isovaleramide may also be formulated into chewing gum.

The isovaleramide active ingredient may also be administered by injection or other systemic routes, such as transdermal or transmucosal (e.g., nasal or rectal) administration. However, since oral administration is much more convenient, this route of administration is preferred.

It is further understood that isovaleramide can be used in combination with other pharmaceutically active ingredients.

For use as a mild sedative to facilitate sleep, the dosage level is on the order of 500–1000 mg per typical adult or about 10–20 mg/kg, generally taken 15–30 min before facilitation of sleep is desired. Oral dosages can be formulated in correspondingly higher concentrations or larger numbers of capsules or tablets can be taken. In this case, also, the isovaleramide may be simply added to foods or beverages consumed before retiring. Persons suffering from insomnia will benefit from these mild sedative effects.

In addition to the use of isovaleramide as a mild anxiolytic or a mild sedative for humans, isovaleramide may also be useful as a mild anxiolytic or mild sedative for domestic or domesticized animals in which excitation is undesirable, such as, but not limited to cats, dogs, birds, horses, cattle, mink, poultry and fish. In such cases, the isovaleramide may be administered by injection or other systemic routes such as transdermal or transmucosal or orally by addition to food or drink. The indicated dosage of isovaleramide per kilogram of body weight of such animals is about 0.15–20 mg/kg, preferably about 0.25–10 mg/kg, depending upon the species of animal and the route of administration. The indicated dosage of isovaleramide per kilogram body weight as a mild sedative for the animals is in the range of about 1.25–20 mg/kg.

The following examples are intended to illustrate, but not to limit, the invention.

EXAMPLE 1

Comparative In Vitro Cytotoxicity of Isovaleramide and Valepotriate Compounds

The valepotriate compounds valtrate, didrovaltrate and acevaltrate were compared with isovaleramide with respect to their effects on various human and murine tumor cell lines. The cells at log-phase growth were treated with various concentrations of test substances for 48 hr. Growth rates were then determined by directly counting cell numbers or by protein determination. $EC_{50}$ is the effective concentration of test substance that inhibited cell growth by 50%.

The results for isovaleramide as compared to the valepotriate compounds are shown in Table 1. As clearly shown, isovaleramide shows no cytotoxicity at the concentration levels at which the valepotriate compounds are highly toxic.

TABLE 1

| Compound | $EC_{50}$ (μg/ml) | | | | | | | |
|---|---|---|---|---|---|---|---|---|
| | BCA-1 | COL-2 | HT-1080 | LUC-1 | KB | KB-V1 | MEL-2 | P388 |
| Valtrate | 0.41 | 0.59 | 0.41 | 2.00 | 0.51 | 0.72 | 0.39 | 0.06 |
| Didro-valtrate | 0.79 | 1.49 | 0.70 | 2.91 | 2.03 | 1.29 | 0.42 | 0.19 |
| Acevaltrate | 1.94 | 2.89 | 2.05 | 4.30 | 2.70 | 2.26 | 0.75 | 0.88 |
| Isovaleramide | >20 | >20 | >20 | >20 | >20 | >20 | >20 | >20 |

EXAMPLE 2

Comparative Effects of Isovaleramide on the CNS Anxiolytic Activity

Isovaleramide and five other compounds were tested for anxiolytic activity in the Vogel Conflict Assay. FIG. 2 shows the anxiolytic indexes of these test compounds, at various dose levels, which were derived from data obtained in the Vogel Conflict (anxiolytic) Assay using male rats. The "anxiolytic index" is defined as the ratio of the number of punished licks of test animals to that of control animals during a 4-min period. An anxiolytic index greater than one indicates anxiolytic ("calmative") activity. In practice, it is considered that significant "calmative" activity is observed when the anxiolytic index is greater than 1.5. Anxiogenic (CNS-stimulant) compounds exhibit their effects on experimental animals as an increased state of vigilance, characterized by an increase in tension, fear, startle reflexes, etc.

Male Sprague-Dawley rats (250–300 g) were deprived of water for 24 hours before testing. The animals were allowed one five-minute period of drinking in the experimental chamber before receiving the test substances at the indicated doses. Thirty minutes later, the animals were returned to the chamber and allowed to drink for one minute without punishment. For the remaining four minutes, a shock was delivered to the drinking spout and the number of punished licks was recorded. Four or five animals were tested in each group.

Isovaleramide injected into rats IP at 500–1000 mg/kg showed an approximate three-fold increase in the number of punished licks over controls, demonstrating that it is clearly anxiolytic ("calmative") at these dose levels (FIG. 2). ("VALIUM" (diazepam) injected at therapeutically effective doses elicits a ten-fold increase in the number of licks.) n-Butyramide and sucrose (which was included in these assays as a control) showed no significant anxiolytic activity at comparable dose levels, whereas n-valeramide and valnoctamide (see FIG. 1) did exhibit significant "calmative" activity at lower dose levels (250 and 50 mg/kg, respectively), thus emphasizing their stronger hypnotic properties and tendencies (valnoctamide was hypnotic in the rats at 250 mg/kg [data not shown in FIG. 2]). N,N-Diethylisovaleramide, the simple N,N-diethyl derivative of isovaleramide (see FIG. 1), exhibited CNS-stimulating (excitant) activity at 50 mg/kg (FIG. 2) and was a potent convulsant in the rats at 250 mg/kg (data not shown in FIG. 2). Thus, isovaleramide is the one compound from this group of test substances which has the best balance of pharmacologically desirable traits for a mild "calmative" (anxiolytic) agent.

Sedative Activity

Sedative activity elicited by a test substance can be observed directly in experimental animals by a decrease in spontaneous locomotor activity, e.g., in open-field observation experiments. In such experiments, test animals are administered the test substance (usually by IP injection) and, after a suitable waiting period (usually 5–30 min), are placed into an open-field test chamber, which consists of a transparent plastic box with a clearly visible grid painted on the bottom (or floor). The numbers of excursions across the floor grids are then counted over a specified time period (usually 1–3 hours) and are subsequently compared with the numbers obtained from similarly treated saline controls. The number of grid crossings counted gives a direct measurement of the general activity level (measured as spontaneous locomotor activity) of each test animal in question. Sedative activity can be expressed as a percentage of the control level of spontaneous locomotor activity as measured by grid crossings per unit time.

Direct observation experiments showed that naive observers could readily identify and distinguish isovaleramide-treated mice (at doses of 250 mg/kg IP) from saline-treated controls on the basis of general activity level alone, even without counting grid crossings. (Very astute observers could also distinguish test animals from controls at a dose level of 100 mg/kg IP.) At higher dose levels (e.g., at 500 and 1000 mg/kg IP), the observed sedative effects were much more pronounced, with the experimental animals (male mice) clearly becoming progressively more heavily sedated as higher dosages were attained. At 1000 mg/kg IP, the isovaleramide-treated animals were clearly sedentary, with their coats very smooth and lustrous.

Figure 3:
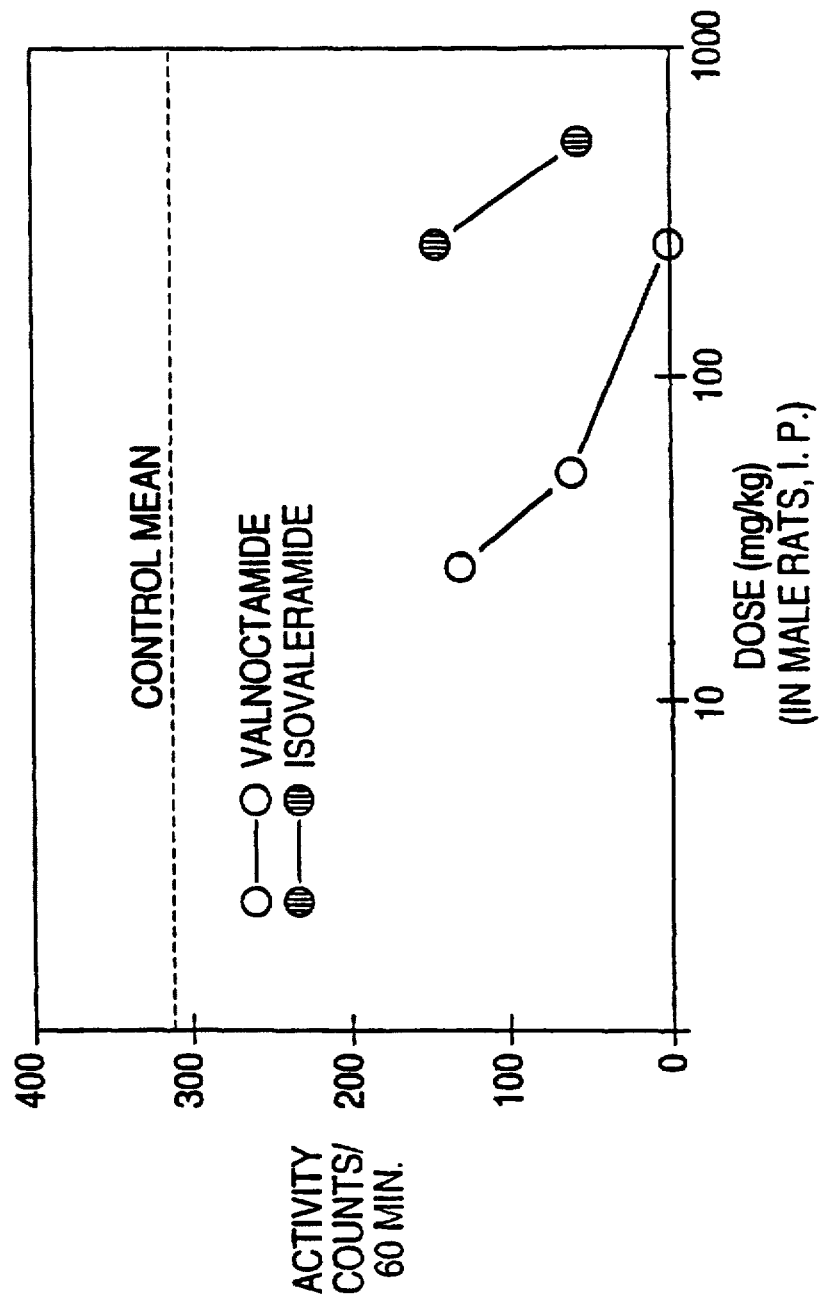
FIG. 3 shows the general sedative effect of isovaleramide as opposed to valnoctamide, demonstrated by electronic measurements of drug-induced decreases in spontaneous locomotor activity in male rats.

General sedative effects can also be measured electronically by recording drug-induced decreases in spontaneous locomotor activity in treated experimental animals, as shown in FIG. 3. The data in FIG. 3 clearly show that valnoctamide is about ten times more potent than isovaleramide as a strong sedative-hypnotic agent. Valnoctamide was hypnotic to the rats at a dosage of 250 mg/kg IP, whereas at the same dose level isovaleramide decreased locomotor activity to a level comparable to that induced by valnoctamide at 25 mg/kg. Similarly, the decrease in locomotor activity induced by isovaleramide at 500 mg/kg IP is comparable to that induced by valnoctamide at 50 mg/kg IP. Thus isovaleramide exhibits only about one-tenth of the potent sedative-hypnotic properties exhibited by valnoctamide at relatively low doses, and is therefore superior to it as a mild "calmative" agent.

Figure 4:
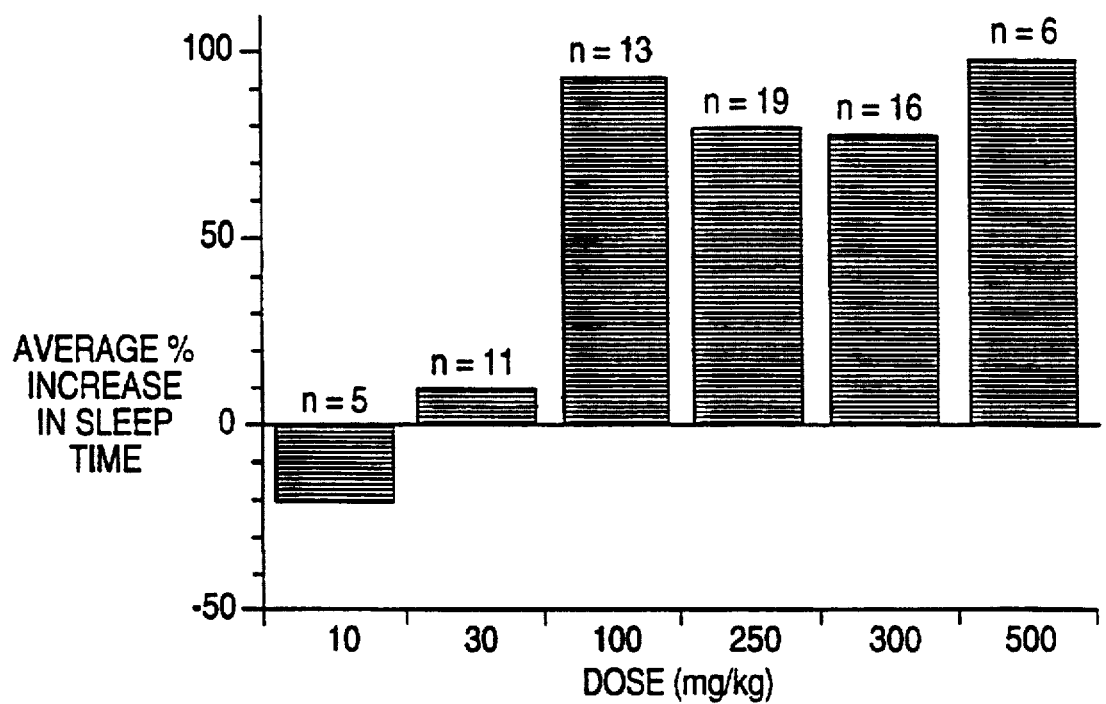
FIG. 4 shows the average relative percent increase in pentobarbital-induced sleep time for isovaleramide-treated mice over control mice.

The CNS-sedative activity of a drug substance can also be demonstrated by a prolongation of the sleep time of pentobarbital-induced sleep. In these assays, experimental animals which are administered a hypnotic dose of a barbiturate (in this case, pentobarbital sodium, 50 mg/kg IP) will sleep for a longer period of time than controls (saline-treated animals) if a drug with sedative properties is co-administered. In our experiments, a sedative effect of isovaleramide could be detected and quantified at dose levels of 30–500 mg/kg IP administered to male Swiss-Webster mice (30–45 g) 30 minutes before receiving the pentobarbital at 50 mg/kg IP (see FIG. 4). Thus, significant sedative effects on the CNS of the experimental animals, as shown by a significant prolongation of the pentobarbital-induced sleep time, could be demonstrated for isovaleramide-treated mice in the dose range of 100–500 mg/kg IP (see FIG. 4).

Weak Hypnotic Activity and Potency

The hypnotic activity of isovaleramide was compared to that of valnoctamide by determining doses (administered to rodents by IP injection) sufficient to induce a loss of the righting reflex and an apparent loss of consciousness and responsiveness ("sleep induction"). Although valnoctamide was hypnotic (i.e., induced sleep) at doses of 250 mg/kg IP in male rats, isovaleramide was not hypnotic in male mice even at 1000 mg/kg IP. However, at the nearly toxic dose level of 2000 mg/kg IP in male mice, isovaleramide exhibited hypnotic activity. Thus, valnoctamide is a much more potent hypnotic than the weakly active isovaleramide, which produces hypnosis only in very large doses approaching toxic dose levels (i.e., greater than 1 g/kg).

Lack of CNS-Stimulating and Convulsant Activities and Other Acutely Toxic Effects Convulsant activity was tested for N,N-diethylisovaleramide and isovaleramide itself. The potential for CNS-stimulating and convulsant properties was assessed by administering appropriate doses of the test substances IP to rodents (male mice and rats). N,N-diethylisovaleramide showed potent CNS-stimulating and convulsant properties at doses of 250 mg/kg IP in male mice and rats; at 500 mg/kg IP in male mice, N,N-diethylisovaleramide caused death following convulsive seizures. On the other hand, isovaleramide itself showed absolutely no CNS-stimulating or convulsant properties at any dose tested in the range 10–4000 mg/kg IP in male mice. At the highest dose of isovaleramide tested (4000 mg/kg IP), some deaths resulted among the test animals (male mice) after sleeping for several days, apparently from respiratory depression. However, this dose level was still below the $LD_{50}$ value of isovaleramide since more than half of the experimental animals survived after sleeping for several days. Further testing of isovaleramide at still higher dose levels was precluded by its solubility limits and the consequently overly large injection volumes required.

We claim:

1. A pharmaceutical composition comprising a predetermined amount of isovaleramide in a dosage form.

2. The pharmaceutical composition of claim 1, wherein said dosage form is suitable for oral administration.

3. The pharmaceutical composition of claim 1, wherein said dosage form is suitable for injection.

4. The pharmaceutical composition of claim 1, wherein said dosage form is suitable for rectal administration.

5. The pharmaceutical composition of claim 1, wherein said dosage form is suitable for transdermal or transmucosal administration.

6. The pharmaceutical composition of claim 2, wherein said dosage form is a solid dosage form that contains from about 100 milligrams to about 1000 milligrams of said isovaleramide.

7. The pharmaceutical composition of claim 6, wherein said dosage form is a solid dosage form that contains from about 500 milligrams to about 1000 milligrams of said isovaleramide.

* * * * *